(12) United States Patent
Arjoonsingh et al.

(10) Patent No.: US 11,841,353 B2
(45) Date of Patent: Dec. 12, 2023

(54) METHOD OF AND APPARATUS FOR SCANNING WITH AN UNDERWATER MASS SPECTROMETER

(71) Applicant: Fugro N.V., Leidschendam (NL)

(72) Inventors: Shiva Prakash Arjoonsingh, Katy, TX (US); Leslie Owuraku Baksmaty, Houston, TX (US); James Charles Doherty, Katy, TX (US); Eric Carroll Lissard, New Iberia, LA (US); Benjamin King, Katy, TX (US); Dickie Martin, Opelousas, LA (US); Gary Martin Sharman, Houston, TX (US); Mark Stevens, Houston, TX (US)

(73) Assignee: Fugro N.V., Leidschendam (NL)

( * ) Notice: Subject to any disclaimer, the term of this patent is extended or adjusted under 35 U.S.C. 154(b) by 185 days.

(21) Appl. No.: 17/601,748

(22) PCT Filed: Apr. 16, 2020

(86) PCT No.: PCT/IB2020/053619
§ 371 (c)(1),
(2) Date: Oct. 6, 2021

(87) PCT Pub. No.: WO2020/234659
PCT Pub. Date: Nov. 26, 2020

(65) Prior Publication Data
US 2022/0146475 A1  May 12, 2022

Related U.S. Application Data

(60) Provisional application No. 62/851,193, filed on May 22, 2019.

(51) Int. Cl.
*G01N 30/88* (2006.01)
*G01N 33/24* (2006.01)
*G01N 33/28* (2006.01)

(52) U.S. Cl.
CPC .......... *G01N 30/88* (2013.01); *G01N 33/241* (2013.01); *G01N 33/2823* (2013.01); *G01N 2030/8854* (2013.01)

(58) Field of Classification Search
CPC .......... G01N 2030/8854; G01N 30/88; G01N 33/241; G01N 33/2823; G01V 9/007
See application file for complete search history.

(56) References Cited

U.S. PATENT DOCUMENTS

| 4,340,391 A | 7/1982 | Demaison et al. |
| 4,913,821 A | 4/1990 | Melcher et al. |

(Continued)

FOREIGN PATENT DOCUMENTS

| WO | 2016157121 A1 | 10/2016 |
| WO | 2017217804 A1 | 12/2017 |
| WO | 2020234659 A1 | 11/2020 |

OTHER PUBLICATIONS

Buffagni et al. ("Development and Test of an AUV for Environmental Monitoring and Asset Integrity in Offshore O&G Scenarios: Clean Sea Project", Society of Petroleum Engineers, SPE International Conference on Health, Safety, and Environment, Mar. 17-19, 2014.) (Year: 2014).*

(Continued)

*Primary Examiner* — Kristina M Deherrera
*Assistant Examiner* — Jean F Morello
(74) *Attorney, Agent, or Firm* — Polsinelli PC

(57) ABSTRACT

The present invention relates to systems and methods for finding and sampling hydrocarbons from seeps in water or from artificial sources of water. The present invention related to systems and methods for in situ analyzing fluid samples in a body of water. The systems and methods can be used to find hydrocarbons and associated non-hydrocarbons from seeps in water. Such seeps may come from natural (Continued)

sources in deep water, possibly as deep as 3000 m or even more.

20 Claims, 8 Drawing Sheets

(56) References Cited

U.S. PATENT DOCUMENTS

| | | | |
|---|---|---|---|
| 5,630,987 A * | 5/1997 | Briggs | G01N 33/1826 |
| | | | 436/178 |
| 9,612,231 B2 * | 4/2017 | Pottorf | G01V 3/08 |
| 2005/0063865 A1 * | 3/2005 | Bonne | B82Y 15/00 |
| | | | 422/68.1 |
| 2016/0272506 A1 | 9/2016 | Jensen | |
| 2018/0067228 A1 * | 3/2018 | Nali | B63G 8/001 |

OTHER PUBLICATIONS

International Search Report and Written Opinion; PCT Application No. PCT/IB2020;053619 dated Oct. 12, 2020.

Wankel, S.D et al., "Abstract of New Constraints on Methane Fluxes and Rates of Anaerobic Methane Oxidation in a Gulf of Mexico Brine Pool Via in Situ Mass Spectrometry", Deep Sea Research Part II: Topical Studies in Oceanography, Pergamon, Amsterdam, Netherlands, vol. 57, No. 21-23, Nov. 1, 2010; pp. 2022-2029; XP027494255.

* cited by examiner

METHOD OF AND APPARATUS FOR SCANNING WITH AN UNDERWATER MASS SPECTROMETER

CROSS-REFERENCE TO RELATED APPLICATIONS

This application is a national stage application of International Application No. PCT/IB2020/053619, which was filed on Apr. 16, 2020, which claims priority to U.S. Provisional Application No. 62/851,193, filed on May 22, 2019, which is incorporated by reference in its entirety.

FIELD OF THE INVENTION

The present invention relates to analyzing fluid samples in bodies of fluid and more specifically to finding and sampling hydrocarbons from seeps in water or from artificial sources of water.

BACKGROUND OF THE INVENTION

The present invention relates to systems and methods for finding and sampling hydrocarbons from seeps in water or from artificial sources of water. In one example, the present invention related to a method for in situ analyzing fluid samples in a body of water. The method is especially useful for finding hydrocarbons and associated non-hydrocarbons from seeps in water. Such seeps may come from natural sources in deep water, possibly as deep as 3000 m or even more. Geochemical samples obtained from natural or artificial seeps address one of the key exploration risks faced in frontier and emerging basins by providing information about the origin, alteration and maturity of any hydrocarbons found.

Water from natural or artificial seeps provide an opportunity to determine the existence, quality and diversity of working petroleum systems in a basin before drilling. For instance, in deep water, surface mounted echo-sounders lack the sensitivity to detect a potentially large class of active seepage that fall below a mass flux threshold. This situation is unlikely to change given growing prohibitions on signal levels in many jurisdictions that are designed to protect marine life as well as physical limitations of existing materials.

Prior art systems designed to detect and/or measure hydrocarbons from seeps in water are, for instance, known from the following documents.

CA 2 853 297 discloses a method for determining a presence, type, quality and/or volume of a subsurface hydrocarbon accumulation from a sample related thereto. The method may include determining a noble gas signature of a sample and at least one or more of determining a clumped isotope signature of the sample and characterizing the ecology signature of the sample. Then, the method integrates signatures to determine information about the subsurface accumulation, such as the location, fluid type and quality, and volume of a subsurface hydrocarbon accumulation.

CN102288719 discloses a system for detecting the methane concentration of seawater in situ. In the system, bottom seawater in a measuring line enters a reducing valve through a filter, so that the pressure of the seawater is lowered to normal pressure. Normal-pressure sample water flows into a gas-liquid separating device after being adjusted by a flow valve. A seawater sample is separated into sample water and sample gas by the gas-liquid separating device. The sample water is collected by a sample water collector. Excessive sample water flows into a waste water compressive cabin. The sample gas is collected by an automatic sample valve, and is conveyed into a gaseous hydrocarbon detection device for testing. The excessive sample gas is emptied, and is adsorbed by chemical adsorption equipment. The sample gas enters the gaseous hydrocarbon detection device. Target gas undergoes a reduction oxidation reaction through a high-sensitivity gas element to generate an electric signal, and the electric signal is transmitted to a Personal Computer on a boat to realize data display. The system detects the methane concentration of a seabed in situ.

WO2018/186738 relates to a sensor arrangement for underwater detection of a leak in a fluid carrying body. A sensor support structure is mountable to a carrier for enabling the sensor support structure to be suitably positioned or moved. A plurality of thermal sensors is distributed on the sensor support structure forming a sensor array. The sensors are provided by optical fibers connectable to an interrogator via optical signal connectors. Each fiber comprises intrinsic fiber optic sensors at respective locations within the fiber, forming the thermal sensors. The fibers are arranged on the support structure such that the intrinsic fiber optic sensors is distributed across the support structure to span a detection area. This document further relates to a method of performing leak detection as well as for discovering natural occurring leaks.

U.S. Pat. Nos. 9,146,225 and 9,612,231 disclose methods for detecting hydrocarbons with an hydrocarbon measurement module equipped with one or more measurement components is described. The method includes navigating the UV within the body of water and monitoring the body of water with measurement components associated with the UV to collect measurement data. The collected data from the UV is used to determine whether hydrocarbons are present at the location.

WO2013/071187 discloses a method for determining a presence, type, quality and/or volume of a subsurface hydrocarbon accumulation from a sample related thereto. The method may include determining a noble gas signature of a sample and at least one or more of determining a clumped isotope signature of the sample and characterizing the ecology signature of the sample. Then, the method integrates signatures to determine information about the subsurface accumulation, such as the location, fluid type and quality, and volume of a subsurface hydrocarbon accumulation.

SUMMARY OF THE INVENTION

Disclosed are systems and methods for hydrocarbon measurements.

The hydrocarbon measurement system, in use, can be deployed close to the seafloor where it can be calibrated under in-situ conditions. In one embodiment, a delay coil enables further samples to be taken from the same or proximate location to where an interesting amount of hydrocarbons was detected without having to return to that location Also disclosed is an underwater vehicle comprising a hydrocarbon measurement system. The underwater vehicle can include a hydrocarbon measurement system configured to combine an acoustic and geochemical approach and, therefore, possessing a very high sensitivity to seepage in conjunction with the capability to take quality controlled samples from sectors of a plume measured to have the highest concentrations.

Disclosed is method for in situ analyzing fluid samples in a body of water including defining a target analyte and a threshold concentration for the target analyte, continuously collecting fluid from the body of water into a fluid circuit, retaining the fluid in the fluid circuit in a time-ordered fashion, measuring the concentrations of the target analyte within the fluid circuit, comparing each of the measured concentrations to the threshold concentration; and when one or more of the measured concentrations is greater than the threshold concentration, and conducting further analysis on the time-ordered retained fluid.

Disclosed are also several calibration methods and a method of use of hydrocarbon measurements.

BRIEF DESCRIPTION OF THE DRAWINGS

Further features and advantages of the invention will become apparent from the description of the invention by way of non-limiting and non-exclusive embodiments. These embodiments are not to be construed as limiting the scope of protection. The person skilled in the art will realize that other alternatives and equivalent embodiments of the invention can be conceived and reduced to practice without departing from the scope of the present invention. Embodiments of the invention will be described with reference to the figures of the accompanying drawings, in which like or same reference symbols denote like, same or corresponding parts, and in which.

DETAILED DESCRIPTION

The present invention will now be described with reference to several embodiments. Reference will be made to an application in seawater. However, the equipment is equally applicable in other waters than seawater, such as rivers and lakes, and in other waters than from natural sources, like man made sources such as infrastructures leaks.

Anatomy of Seeps in Deep Water

The systems and methods described below can locate, quantify and sample dissolved hydrocarbons from deep water active vents that are not visible from the surface. In one example, each sample meets or exceeds a user defined threshold of quality based on concentrations of light hydrocarbons required to determine thermal maturity, mixing and alteration. Active hydrocarbon vents constitute the epicenter of natural seeps and finding them provides access to the clearest signals of hydrocarbon maturity, origin and quality.

Figure 1A:
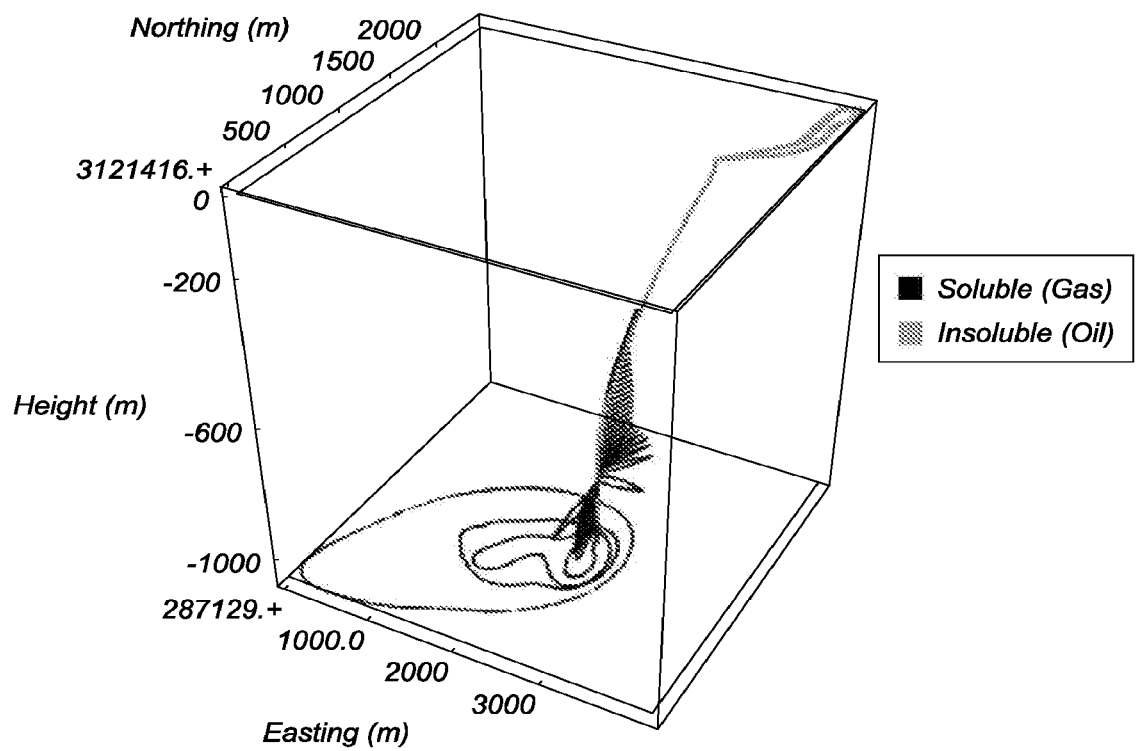
FIGS. 1A-1C show several schematic pictures of hydrocarbon plumes in water above a seep in the bottom, in accordance with an example embodiment.
Figure 1B:
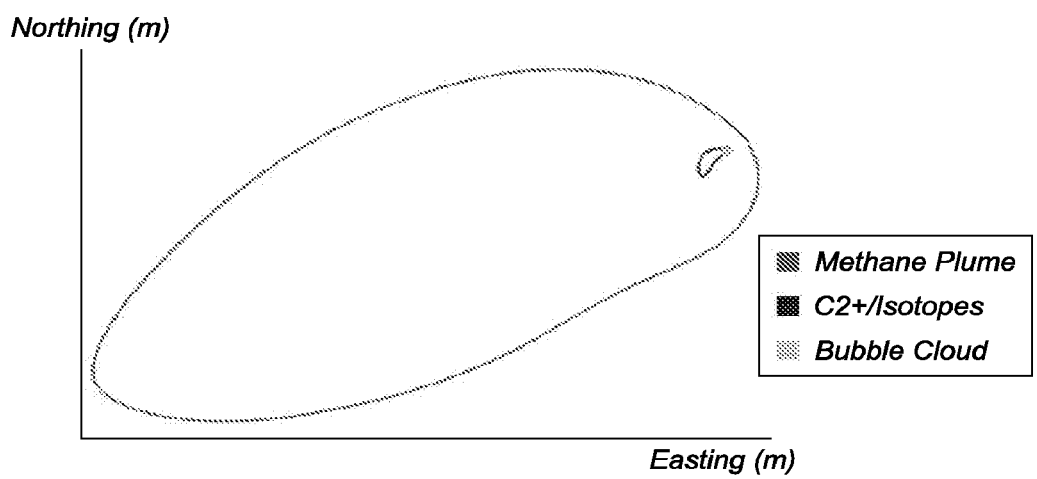
Figure 1C:
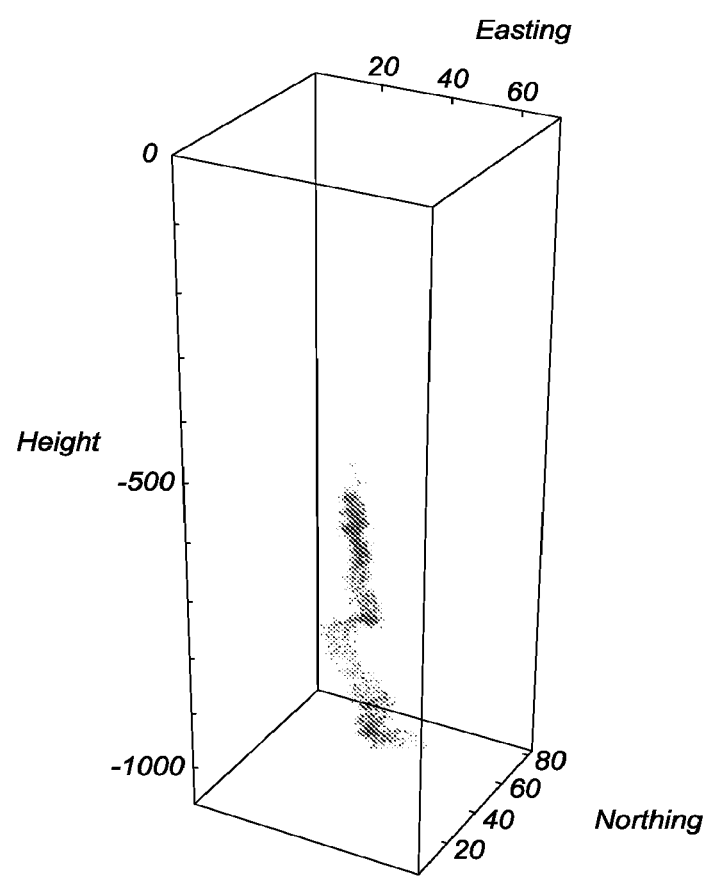

In some embodiments, gas is used as a proxy for finding oil. The quantitative analysis and data presented in FIGS. 1A-C shows this in more detail. These FIGS. show the geochemical and physical footprint of a seep after leaving the mud-line. The migrating hydrocarbons can create a signature in the water column observable both acoustically and geochemically. The systems and methods that are explained in detail below with reference to FIGS. 2-3 may use both approaches to locate, quantify the hydrocarbon content and take a sample that, preferably, meets a user definable quality threshold.

The term "certified solution of hydrocarbons" will be used in the description to refer to a known or reference solution of hydrocarbons. These terms will be interchangeable.

The term "in situ," is defined as collecting and analysing fluid samples within the body of water. Samples may be collected by a subsurface vehicle, for example, by a manned or unmanned underwater vehicle. The samples may be analyses in the subsurface vehicle or on a surface vessel through a continuous line from the subsurface.

FIG. 1A shows a schematic picture of an example of a dissolved hydrocarbon plume in the water column. It originates from upward migrating bubbles and droplets and is invisible to the eye. It can be detected by analytical instruments, for example, a mass spectrometer, Raman spectroscopy, isotopes probes, and/or a fluorometer contained within the system of the present invention. The insoluble components that form the surface slick are also observable by radar.

FIG. 1B shows a map view of an example dissolved hydrocarbon plume at 10 m above the seafloor. In this example, the area for which isotopes or C2+ (i.e., hydrocarbon molecules with more than 2 C atoms) can be detected from samples brought to the laboratory is 0.3% of the vast area over which only methane may be observed. This underscores the desire to be able to properly position the system components before sampling.

FIG. 1C shows an acoustic image in the water column as produced by using a high frequency forward looking M3 sonar that followed a bubble cloud in a real world environment from the seafloor until it was no longer visible.

In some embodiments, seeping oil can migrate from the subsurface and can separate into liquid and gas phases due to the lower pressure at the seafloor, as compared to the reservoir. The acoustic and geochemical instruments are capable of measuring the gas content of the gas phase. Field observations and physics suggest that slicks are associated with bubble clouds within the water column and that the gas provides the buoyancy that focus the initial pooling of oil on the surface before subsequent spreading by currents.

The system of the present invention is designed to locate, characterize and sample migrating hydrocarbons in deep water and filling some of these gaps. To more fully appreciate the value proposition of the present system a quantitative picture of the fate of hydrocarbons in the water column is presented here. Key properties of seeps within the water column are:

The geochemical signal is strongest at the seafloor and decreases rapidly with height from the mud-line until the soluble material in the droplets and bubbles dissolve. In FIG. 1a, it is quite clear why controlled access to the seafloor would open up the opportunity to a much higher signal quality. First however, one needs to locate these vents. The system described here can do this both geochemically or acoustically.

The dissolved hydrocarbons are dominated in concentration by methane, ethane, propane, butane and pentane (C1-C5). Their relative concentrations and the abundances of the stable isotopes of carbon and hydrogen within them provide maximal information on origin, mixing and alteration of the migrating hydrocarbons. In FIG. 1b one can see the huge challenge in locating samples containing C2+ or isotopic abundance. Since the plume is time dependent the ability to quickly map it and locate the most prospective area dramatically increases the chances of providing information about C2+ and isotopes. In FIG. 1b the ratio of the region where isotopes or C2+ are above detection is only about 0.3% of the area where methane is detectable.

The bubble composition changes slowly with height from the mud-line till complete dissolution. In some examples, samples are taken at the mud-line for a more accurate measurement of molar ratios. Moreover, it is arranged to perform in-situ measurements which offers a great advantage because samples collected at the seafloor lose a great deal of material due to the drop in pressure during transit to the surface.

In the shown example, the bubble/droplet cloud is a few meters wide and towers over the entire water column save for the last 400 meters before the surface. FIG. 1c presents an acoustic image taken from a high frequency sonar which shows the individual scatters. For a constant mass flux, active vents become more difficult to see from the surface with increasing depth. This is due to both the increased density of the gas which implies fewer bubbles, and the greater attenuation of the acoustic beams due to increased travel distances. The geochemical signal at the seafloor however remains within the same order of magnitude notwithstanding the fewer number of bubbles due to the increased solubility of gas with pressure. For example, in a water column of 3000 m a seep that was detectable from the surface in a water column of 1000 m could become invisible from the surface even as the geochemical detection range at the seabed remains roughly the same. Therefore, in an embodiment, the system as presented here is provided with one or more suitable acoustic sensors that have high acoustic sensitivity to the bubble cloud because they can be located in close proximity to the seafloor.

Surface slicks are also an excellent way to detect active migration within a radius that is a few multiples of the water depth. However, there is evidence that there are many more bubble clouds than there are slicks. The physics of the problem also suggest that slick formation is a function of water depth, ocean currents and surface conditions. Therefore, the system of the present invention is arranged such that it can quickly locate and provide preliminary samples from one or more emission points on the seafloor where there are confirmed slicks or search in regions for which there are indications but no direct evidence of bubble clouds from the surface.

By collecting fluid samples from a body of water (e.g., on a continuous basis), the concentration of a target analyte (e.g., methane, etc.) can be measured and compared to a threshold concentration (e.g., from background concentrations, etc.). When the measured concentration exceeds the threshold concentration, the time-ordered retained fluid can be further analyzed (e.g., to determine another analyte (e.g., C2, C3, etc.). In this example, a more accurate decision can be made regarding the presence of an active seep and the likelihood of its connection to reservoired hydrocarbons.

Total System Setup

Figure 2:
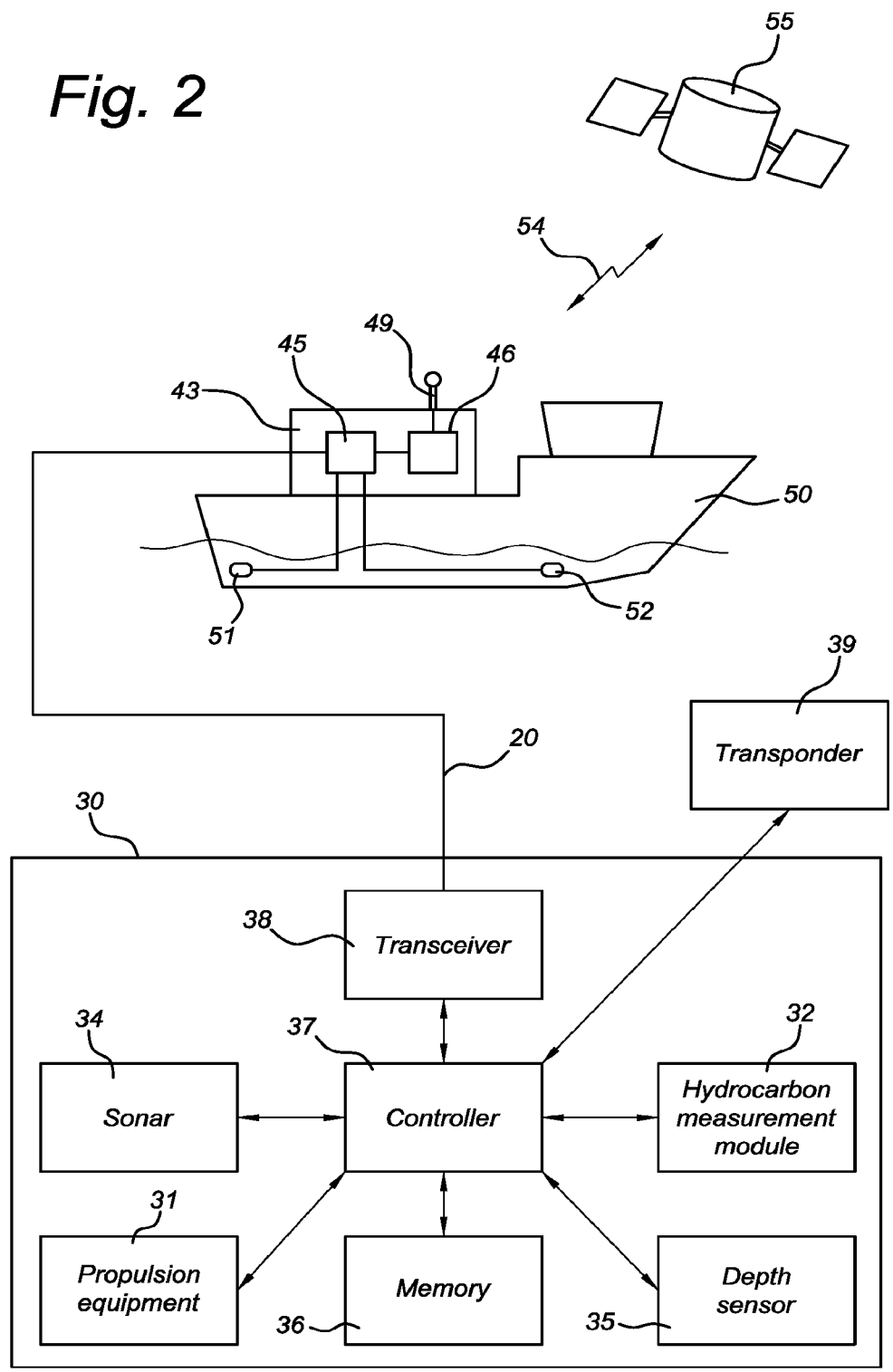
FIG. 2 shows a schematic view of the total system setup, in accordance with an example embodiment.

FIG. 2 illustrates a system for the detection of a seep (e.g. a seafloor, etc.) and analyzing hydrocarbons present in the seep. The system comprises a survey ship 50 from which a remotely operated vehicle 30 can be operated (e.g., via cable 20, wirelessly, etc.). In some examples, cable 20 can comprise one or more optical fibers for transmission of optical signals between the survey ship 50 and the remotely operated vehicle 30. In other examples, a copper wire or any other suitable communication cable may be applied. In other examples, wireless transmission between survey ship 50 and remotely operated vehicle 30 is possible.

The remotely operated vehicle 30 can comprise a controller 37 which is connected to a transceiver 38 that enables communication with the survey ship 50. Coordination between the on-board elements of the remotely operated vehicle 30 cab be provided via the controller 37.

The controller 37 can connected to a sonar 34, propulsion equipment 31, memory 36, a depth sensor 35, a hydrocarbon measurement module 32, and a transponder 39. In some examples, equipment used in remotely operated vehicles can also be included.

Controller 37 may be implemented by any suitable computer device known in the art, for example, as shown in FIG. 7. Memory 36 can store suitable computer programs with instructions and data configured to be loaded by controller 37 which, by running the programs, performs functions as explained, below, in greater detail. In some examples, controller 37 may be one or more computer devices. In some examples, controller 37 may be implemented within hydrocarbon measurement module 32. In some examples, a portion of controller 37 can be used to control hydrocarbon measurement module 32 and may be located within hydrocarbon measurement module 32, while another portion can be implemented within the remotely operated vehicle 30, but outside of the hydrocarbon measurement module 32.

The survey vessel 50 is equipped with a controller 45 which, in this embodiment, is connected to a global positioning system, GPS, 46 and to two transducers 51, 52. In other embodiments, the survey vessel may comprise only one transducer. In other embodiments, the survey vessel may comprise more than two transducers. GPS 46 is connected to an antenna 49 to enable communication with one or more satellites 55. Transducers 51, 52 may be located on different areas underneath the hull of the vessel 50. Controller 45 may be implemented by more than one computer device configured to communicate with one another.

Controller 45 may be implemented by any suitable computer device known in the art, for example, as shown in FIG. 7. Memory 45 can store suitable computer programs with instructions and data configured to be loaded by controller 45 which, by running the programs, performs functions as explained, below, in greater detail. In some examples, controller 37 may be one or more computer devices. Controller 45 can be connected to one or more devices on the ship, for example to displaying information or data, including one or more printers and one or more monitors (not shown).

In some embodiments, remotely operated vehicle 30 is configured to automatically determine its position using transponder 39. For example, the transducers can send acoustic pulses to the transponder 39. A synchronization signal can also be provided (e.g., optical fibers of cable 20, wirelessly, etc.) to the controller 37 of the remotely operated vehicle 30. By synchronizing controller 45 on board of survey vessel 50 with controller 37 via a clock signal, the transmission and receipt times of the acoustic pulses from the transducers can be accurately recorded, and the relative location of remotely operated vehicle 30 with respect to the survey vessel 50 may accurately be determined (e.g., by triangulation of the signals, etc.). By associating the GPS signal 54 (e.g., received via its antenna 49) with the relative location of the remotely operated vehicle 30, the exact, "absolute" location (in relation to the earth) of the remotely operated vehicle 30 can be determined.

The propulsion equipment 31 can be used by the remotely operated vehicle 30 to position itself on or move to a desired location. Positioning control signals may be generated by controller 45 on board of survey vessel 50 (e.g., automatically, instructed by an operator, etc.) and then transmitted to controller 37 which is configured to control propulsion equipment 31 based on the positioning control signals. In some examples, controller 37 may be configured to read pre-stored positioning control signals (e.g., instructions and data) from memory 36 which enables automatic movements of remotely operated vehicle 30 along one or more predetermined trajectories. In other examples, the control signals can be derived from the received information (e.g., GPS, positioning, etc.).

Depth sensor 35 can measure the depth of remotely operated vehicle 30. Depth signals (e.g., from the depth sensor) can be sent to controller 37 which is configured to send the depth signals to controller 45. The depth signals can be used to determine and display the depth of remotely operated vehicle 35 at the survey vessel 50 (e.g., monitors, etc.). In some examples, one or more other sensors can be used to determine a state of the remotely operated vehicle 30 (e.g., temperature sensor, speed sensor, etc.).

Acoustic sensor 34 (e.g., sonar sensor, etc.) can be configured to collect bathymetry and backscatter data, and send such data to controller 37. Acoustic sensor 34 can be configured to accurately, precisely, and reliably determine the origin of an acoustic flare created by a gas bubbler. In some embodiments, based on data received from acoustic sensor 34, controller 37 is configured to locate a gas bubbler within a specific amount of meters (e.g., 5 meters, 10 meters, 20 meters, etc.) of its actual location from a maximum altitude sonar grid.

Hydrocarbon measurement module 32 is configured to collect samples of water at actual locations of remotely operated vehicle 30 and measure hydrocarbon content in these samples, as will be explained in detail hereinafter.

Hydrocarbon Measurement Module

Figure 3:
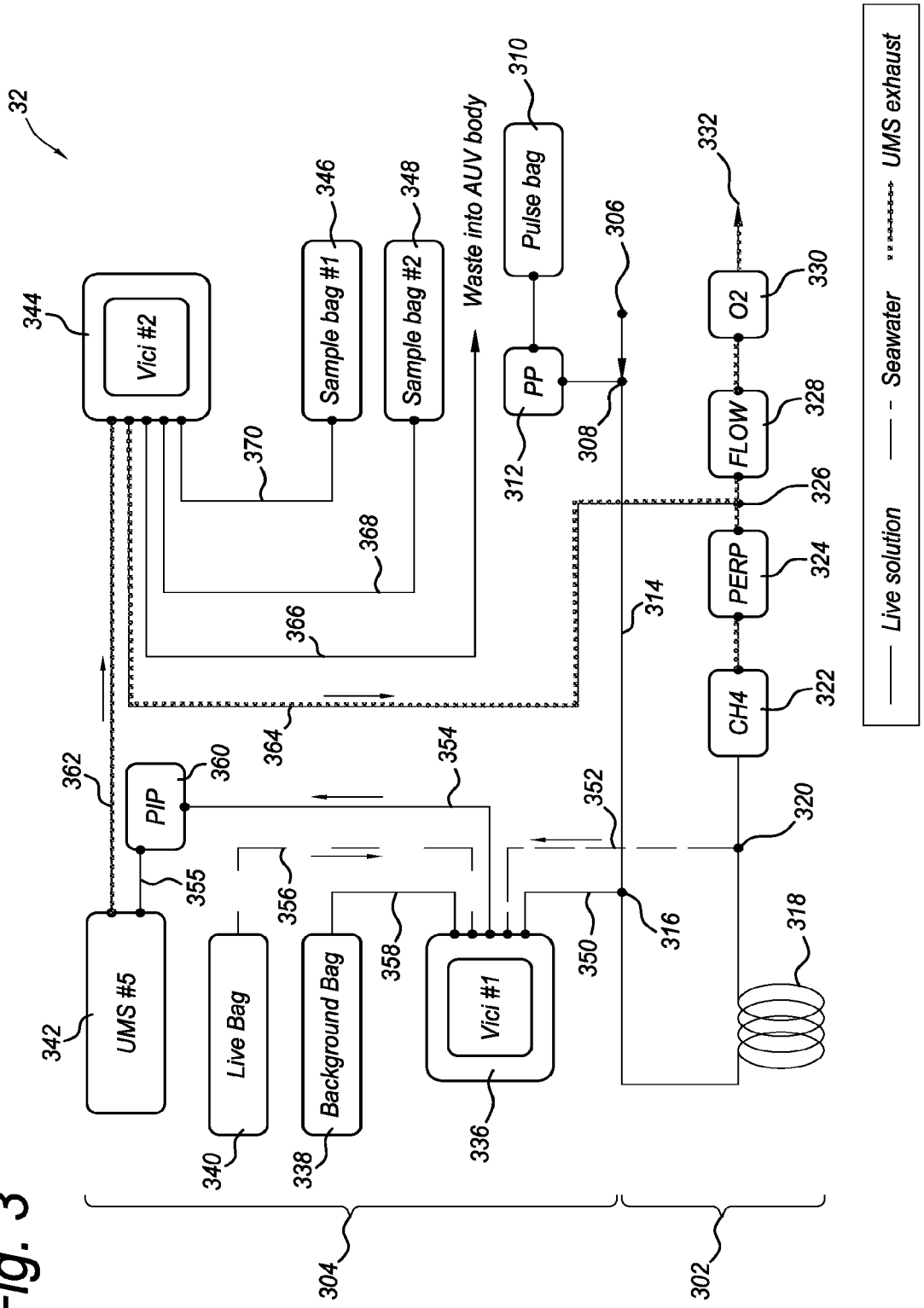
FIG. 3 shows a block scheme of a hydrocarbon measurement system, in accordance with an example embodiment.

Hydrocarbon measurement module 32 is explained in detail with reference to FIG. 3. Hydrocarbon measurement module 32 can comprise a main loop 302 and a sensing loop 304. The main loop 302 and sensing loop 304 can comprise one or more conduits. The conduits may be implemented in several different ways (e.g., rigid or flexibles pipes, hoses, etc.). The conduits may be made of any suitable material including metals and plastics.

The main loop 302 comprises a main conduit 314 having an inlet 306. The main conduit 314 has a junction 308 (adjacent to the inlet 306) connected to an outlet of a pump 312 (e.g., via a suitable conduit, etc.). An inlet of pump 312 is connected to an outlet of a pulse bag 310 (e.g., via a suitable conduit).

Main conduit 314 can end at an inlet of a methane measurement device 322. Upstream from methane measurement device 322, main conduit 314 can comprise a postcoil junction 320, a delay coil 318 upstream from post-coil junction 320, and a pre-coil junction 316 upstream from delay coil 318. Downstream from methane measurement device 322, main loop 302 comprises a main loop pump 324 having an inlet connected to an outlet of methane measurement device 322 (e.g., via a suitable conduit), a flow measurement device 328 having an inlet connected to an outlet of main loop pump 324 (e.g., via a suitable conduit), and an oxygen measurement device 330 having an inlet connected to an outlet of flow measurement device 328 (e.g., via a suitable conduit). Main loop 302 can have an outlet 332 (e.g., an outlet of oxygen measurement device 330). In some examples, flow measurement device 328 and oxygen measurement device 330 can be interchanged as to their location (e.g., as seen in the flow direction). The conduit connected to the outlet of main loop pump 324 can have a junction 326 connected to sensing loop 304. The main loop pump 324 can be configured to pull water through the main conduit 314. In some embodiments, the flow measurement device 328 may be used to perform an independent check on the function of the main loop pump 324. In some examples, the oxygen measurement device 330 may be used to perform a gross error check.

In some embodiments, sensing loop 304 can comprise a first switchable valve device 336, a background back 338, a live bag 340, an underwater mass spectrometer 342, a pump 360, a second switchable valve device 344, a first sample bag 346, and a second sample bag 348. In some embodiments, more than two sample bags may be utilized. The methane measurement device 322 may be used as a gross error check against the data from the underwater mass spectrometer 342 by correlating data coming from both devices.

In some examples, live bag 340 can comprise a known solution of hydrocarbons, and background bag 338 can comprise a known solution of sea water (e.g., of a predetermined composition, etc.). These bags (e.g., 340, 338) can be used in a sensitivity calibration of underwater mass spectrometer 342.

In some embodiments, first switchable valve device 336 has a first inlet connected to pre-coil junction 316 of main conduit 314 (e.g., via a conduit 350); a second inlet connected to post-coil junction 320 of main conduit 314 (e.g., via a conduit 352); a third inlet connected to an outlet of live bag 340 (e.g., via a conduit 356); a fourth inlet connected to an outlet of background bag 338 (e.g., via a conduit 358); and an outlet connected to an inlet of pump 360 (e.g., via a conduit 354).

In some examples, pump 360 has an outlet connected to an inlet of underwater mass spectrometer 342 (e.g., via a conduit 355). Underwater mass spectrometer 342 can have an outlet connected to an inlet of second switchable valve device 344 (e.g., via a conduit 362). Second switchable valve device 344 can have a first outlet connected to junction 326 of main loop 302 (e.g., via a conduit 364); a second outlet connected to a conduit 366 which has an outlet for draining waste inside a suitable location of remotely operated vehicle 30; a third outlet connected to an inlet of second sample bag 348 (e.g., via a conduit 368); and a fourth outlet connected to an inlet of first sample bag 346 (e.g., via a conduit 370).

In some examples, pulse bag 310 can contains a solution of hydrocarbons (e.g., calibrated, certified, etc.) for in-situ calibration of underwater mass spectrometer 342 and for pulse generation (e.g., to measure the impulse response for various configurations of flow in main loop 302). Pump 312 may be a piston pump which can be activated by controller 37 (via wireless and/or wired communication technologies), to receive a short pulse of a high concentration of hydrocarbons from pulse bag 310 and pump that short pulse into an inlet stream of sea water to main conduit 314 (e.g., via junction 308). Controller 37 can simulate an impulse or step function of an amount of hydrocarbons in seawater entering the system via inlet 306.

In some embodiments, delay coil 318 can be arranged in main conduit 314. In some examples, the coil is shaped like a coil of a predetermined length. In these embodiments, a coil can introduce a predetermined extra travel, or delay, time of a certain amount of liquid (e.g., here seawater with or without hydrocarbons) flowing from pre-coil junction 316 to post-coil junction 320. When the travel speed (e.g., of the liquid through the coil) is known, the travel time can be determined (based on the length) and the delay time between pre-coil and post-coil junctions (e.g., 316, 320) can also be determined. In other examples, main conduit 314 may be arranged in a zig-zag pattern between pre-coil and post-coil junctions (e.g., 316, 320) such that the main conduit has a predetermined length between them. While the delay device in this example is a coil, other delay devices are contemplated, for example (but not limited to) a rigid pipe conduit or a carved path in a solid block.

In some examples, methane measurement device 322 may be implemented by a Franatech Laser based Methane Sensor. Methane measurement device 322 can be configured to provide (e.g., via wireless or wired communication) a methane measurement signal to controller 37. In response to the signal, controller 37 can derive a methane percentage in the sea water flowing through measurement device 322.

In some examples, pump 324 may be implemented as a heavy duty subsea peristaltic pump configured to generate a steady laminar flow though main loop 302. Pump 324 can be controlled by controller 37 (e.g., via including wireless and/or wired communication technologies).

In some examples, flow measurement device 328 is configured to monitor the flow of liquid through an enclosed space. Flow measurement device 328 can be configured to provide (e.g., via wireless or wired communication) a flow measurement signal to controller 37. In response to receiving the signal, controller 37 can derive a flow speed and/or flow amount of sea water (e.g., flowing through main conduit 314). Flow measurement device 328 can be used for monitoring the flow of liquid through the conduit 314. In some examples, the pump 324 can have its speed controlled (e.g., by revolutions per minute). Changes in the speed of the pump 324 may be confirmed by monitoring the flow (e.g., via flow measurement device 328). In this way, the flow measurement device 328 may be used to verify the flow rate through the delay coil is constant and that calibrations depending on a steady flow rate are still valid (e.g., during time the system is deployed). In some examples, the delay time introduced by the delay coil 318 can be measured on-site.

In some examples, oxygen measurement device 330 may be an Anderaa Oxygen Optode Sensor. Oxygen measurement device 330 can be configured to provide (e.g., via wireless or wired communication) an oxygen measurement signal to controller 37. In response to receiving the signal, controller 37 can derive an oxygen percentage in the sea water. Oxygen is usually displaced in hydrocarbon emissions. The oxygen measurement device 330 may be used for detecting a drop in O2 which may be used as a form of gross error check (e.g., when methane is found). In some examples, the oxygen measurement device 330 may be used to verify measurement from the underwater mass spectrometer 342 (e.g., which also measures dissolved oxygen). Discrepancies between the oxygen measurement device 330 and the underwater mass spectrometer 342 may be an indication of a problem with the underwater mass spectrometer 342 (which needs to be diagnosed and corrected).

In some embodiments, switchable valve device 336 can be a valve device programmatically switched by controller 37 to control an amount of a sample taken from main conduit 314 (e.g., at the location of pre-coil junction 316, at the location of post-coil junction 320, both, etc.). In some examples, conduit 352 may be larger than conduit 350 such that a sample taken from main loop 302 at the location of post-coil junction 320 is larger than a sample taken from main loop 302 at the location of pre-coil junction 316. However, the invention is not restricted to such an embodiment. It may be the opposite or such samples may have equal size.

In some examples, switchable valve device 336 may be controlled to receive a portion of a calibrated solution of hydrocarbons (e.g., as contained in live bag 340 for in-situ calibration of underwater mass spectrometer 342). In some examples, switchable valve device 336 can be controlled to receive an amount of liquid from live bag 340 (e.g., for pulse generation of a certain amount of flow of liquid towards underwater mass spectrometer 342 via conduit 354 to enable measurement of the impulse response by underwater mass spectrometer 342 for various configurations of flow in sensing loop 304).

In some examples, switchable valve device 336 can be switched to receive a predetermined amount of sea water from background bag 338 (e.g., via conduit 358).

In some examples, switchable valve device 336 is configured to switch any one of its inlets to its outlet which is connected to mass spectrometer 342 via pump 362 (e.g., via respective conduits 354 and 355). In some examples, switchable valve device 336 is connected to controller 37 (e.g., via wireless and/or wired communication technologies).

In some examples, pump 360 can be a piston pump that maintains flow in the sensing loop. Controller 37 can control pump 360 (e.g., via wireless or wired communication).

In some examples, underwater mass spectrometer 342 can be an underwater mass spectrometer capable of measuring hydrocarbons, at least including light hydrocarbons with a Molecular Mass<92 atomic mass unit (amu) and up to at least 200 amu. Spectrometer 342 can be configured to send a measurement signal to controller 37, indicating an amount of hydrocarbons in the received sample of seawater. Controller 37 and data indicating the amount can be transmitted to controller 45 of survey vessel 50. Controller 45 can then display this information at the vessel, for example, via one or more printers and one or more monitors (not shown).

In some examples, switchable valve device 344 is a valve device that can be programmatically switched by controller 37 (e.g., via wireless or wired communication) to receive an amount of sea water flowing in sensing loop 34 (e.g., as received from underwater mass spectrometer 342 via conduit 362 after underwater mass spectrometer 342 has processed received seawater from pump 360 and has measured hydrocarbon content). In some examples, switchable valve device 344 can switch (e.g., via controller 37) its internal valves such that seawater incoming via conduit 362 is exhausted via at least one of conduits 364, 366, 368 and 370.

It is observed that, in the embodiment explained here, remotely operated vehicle 30 has one controller 37. However, as indicated above there may be more controllers each one having, e.g., a dedicated task. For instance, there may be a separate controller 20 installed in the hydrocarbon measurement module 32 taking care of all its functions, which separate controller is configured to communicate with controller 37 in any suitable way, including via a wireless and/or wired connection such that data and control signals can be exchanged with controller 45 on board of survey vessel 50.

Functioning of the System

In some embodiments, remotely operated vehicle 30 can traverse through a hydrocarbon plume (e.g., originating from the seafloor). Vehicle 30 can experience successive regions of high and low hydrocarbon concentration as it navigates in an out of the plume. In some examples, vehicle can operated at high speeds and with the focused nature of plumes, pulses of hydrocarbons in incoming seawater can be short and irregularly spaced. Hydrocarbon measurement module 32 enables detection and precise tracking of these pulses that enter the hydrocarbon measurement module 32.

For example, precise pulse tracking and trapping is greatly improved when the flow throughout the entire hydrocarbon measurement module 32 generated by pumps 324 and 360 is steady and laminar. In some embodiments, pump 324 is controlled (by controller 37) to drive a continuous laminar flow (e.g., 500 ml/min+/−10%) from the sea outside remotely operated vehicle 30 into delay coil 318 and back out again via outlet 332. In some examples, the laminar flow may be in a range of 100-5000 ml/min. In other examples, the laminar flow may be in a range of 100-2000 ml/min. Pump 360 (in sensing loop 304) can also be controlled (by controller 37) to drive a much smaller flow (e.g., 10 ml/min+/−10%) through sensing loop 304. In some examples, samples can be continuously extracted from the contents of the flow of seawater in main loop 302. The sample amount may, for example, in a range of 1-100 ml/min. In other examples, the range can be 2-20 ml/min Calibration Timing Calibration The hydrocarbon measurement module 32 is configured to perform calibration of its functioning at the site of operation, (e.g., at the bottom of the sea, 3000 meter below sea level, etc.). This is advantageous because temperature and pressure have a significant influence on the timing and accuracy of the hydrocarbon measurements performed by the underwater mass spectrometer 342, and temperature and pressure cannot be predicted accurately before the actual measurements are performed.

The attached bag 310, 340 can contain certified solutions of hydrocarbons which are be used to generate artificial pulses of hydrocarbons within the system to precisely measure the travel times between junctions of interest as well as the system sensitivity to hydrocarbons of interest. In so doing the system can accurately track and trap pulses of high concentration for detailed analysis ("gulping"). A corollary of precise tracking is the ability to pinpoint where in the water the pulse was encountered which leads to the capability to locate precisely a chemical plume in the water.

The speed of flow of seawater flowing through main loop 302 can depend on the pumping force of pump 324. The speed of flow of seawater flowing through sensing loop 304 can depend on the pumping force of pump 360. At least two travel times of the seawater are important: first, the travel time of the seawater between inlet 306 and underwater mass spectrometer 342 via pre-coil junction 316, and second, the travel time of the seawater between inlet 306 and underwater mass spectrometer 342 via post-coil junction 320 as delayed by delay coil 318. These travel times, for example, should be known to calculate at which time and location, inlet 306 received a certain amount of hydrocarbons in the incoming seawater. To calculate the location where inlet 306 received a certain amount of hydrocarbons in the incoming water, controller 37 should know the speed of hydrocarbon measurement module 32 (e.g., in directions as a function of time). This speed is equivalent to the speed of remotely operated vehicle 30 (if they are firmly attached to one another).

Figure 4A:
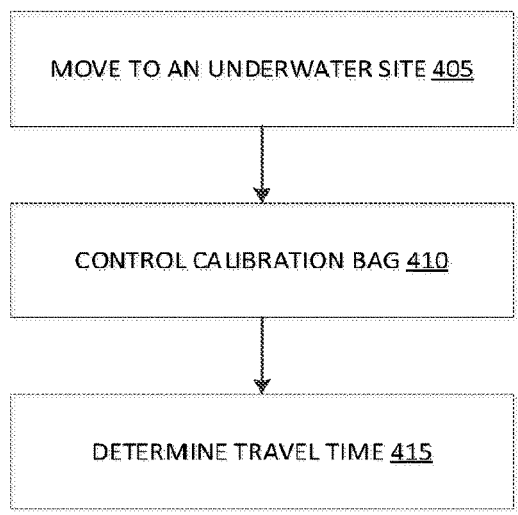
FIG. 4A-E show a flow diagram of example methods of calibration, in accordance with an example embodiment.

A method of determining travel time of hydrocarbons entering the module at inlet 306 and flowing to underwater mass spectrometer 342 in an in-situ sensitivity calibration is illustrated below and in FIG. 4A.

At block 405, the hydrocarbon measurement module 32 can be moved to an underwater site;

At block 410, the timing calibration bag 310 can be controlled to provide at least a portion of its certified solution of hydrocarbons to the inlet 306 during an in-situ timing calibration; and At block 415, at least a travel time is determined from the certified solution of hydrocarbon flowing from the inlet 306 to the mass spectrometer 342.

In some examples, in-situ timing calibration can include one or more of the following actions:

(i) moving the hydrocarbon measurement module to an underwater site,
(ii) controlling the timing calibration bag 310 to provide at least a portion of the certified solution of hydrocarbon to the inlet 306 during the in-situ timing calibration in which at least a travel time is determined from the certified solution of hydrocarbon flowing from the inlet 306 to the mass spectrometer 342 either via the first conduit 350 or the second conduit 352.

Figure 4B:
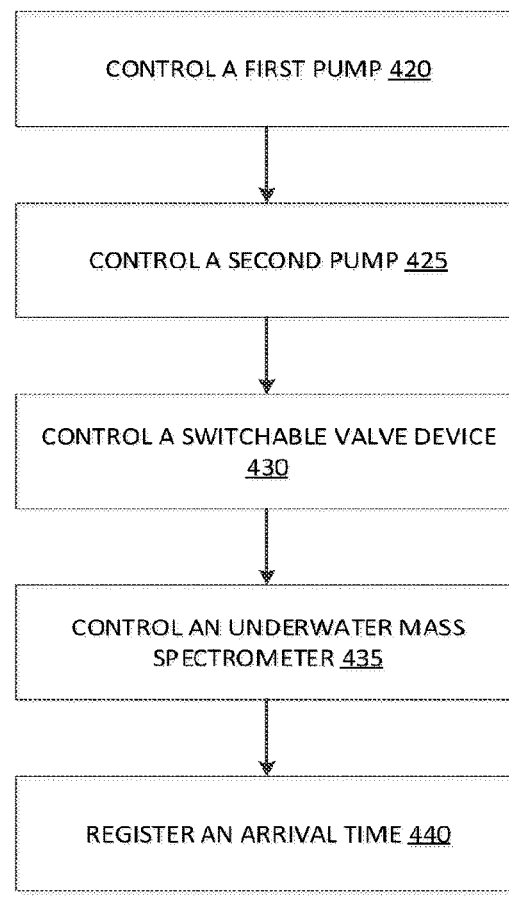

In some examples, relevant travel times can be measured by controller 37 as illustrated in the method below and in FIG. 4B.

At block 420, controller 37 can control pump 324 to pump seawater through main loop 302;

At block 425, controller 37 can control pump 312 to provide an amount of the hydrocarbon solution content of pulse bag 310 into main conduit 314 at a first starting time;

At block 430, controller 37 can control switchable valve device 336 to connect conduit 354 to pre-coil junction 316 via conduit 350 and controlling pump 360 to pump a sample amount of seawater from main conduit 314 to underwater mass spectrometer 342 via precoil junction 316;

At block 435, controller 37 can control underwater mass spectrometer 342 to measure hydrocarbon content in the sample amount flowing through underwater mass spectrometer 342 and at block 440, controller 37 can register a first time of arrival of hydrocarbons originating from measuring the hydrocarbon solution content of pulse bag 310.

This first time of arrival is compensated for a measurement time needed by the underwater mass spectrometer 342 to detect the hydrocarbon content, which measurement time may be considerable. This measurement time is known in advance and may depend on the hydrocarbon concerned. Registering a first travel time of the hydrocarbons between pulse bag 310 and underwater mass spectrometer 342 as the time difference between this first time of arrival and the first starting time. Assuming the pump 312 and pulse bag 310 are located very close to the inlet 306, then this first travel time is about the same as the travel time of seawater between inlet 306 and underwater mass spectrometer 342 via pre-coil junction 316.

Figure 4C:
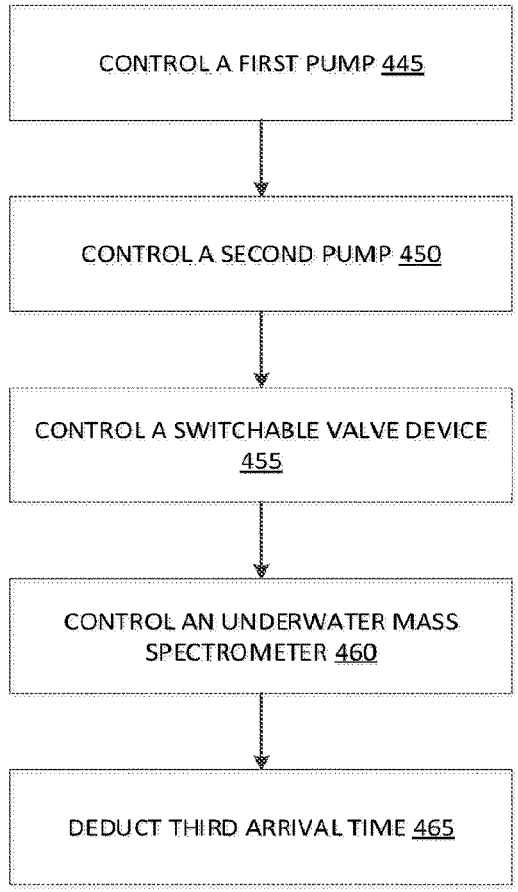

In other examples, controller 37 can repeat the method in FIG. 4B for a second starting time to register a second time of arrival and as illustrated below and in FIG. 4C deducting a third travel time At block 445, controller 37 can control pump 324 to pump seawater through main loop 302;

At block 450, controller 37 can control pump 312 to provide an amount of the hydrocarbon solution content of pulse bag 310 into main conduit 314 at a second starting time;

At block 455, controller 37 can control switchable valve device 336 such that conduit 354 is connected to post-coil junction 320 via conduit 352 and controlling pump 360 to pump a sample amount of seawater from main conduit 314 to underwater mass spectrometer 342 via post-coil junction 320;

At block 460, controller 37 can control underwater mass spectrometer 342 to measure hydrocarbon content in the sample amount flowing through underwater mass spectrometer 342 and registering a second time of arrival of hydrocarbons originating from the hydrocarbon solution content of pulse bag 310. This second time of arrival is compensated for a measurement time needed by the underwater mass spectrometer 342 to detect the hydrocarbon content, which measurement time may be considerable. This measurement time is known in advance and may depend on the hydrocarbon concerned. Registering a second travel time of the hydrocarbons between pulse bag 310 and underwater mass spectrometer 342 as the time difference between this second time of arrival and the second starting time. Assuming the pump 312 and pulse bag 310 are located very close to the inlet 306, then this second travel time is about the same as the travel time of seawater between inlet 306 and underwater mass spectrometer 342 via pre-coil junction 320;

At block 465, controller 37 can deduct the first travel time from the second travel time, resulting in a third travel time which, when assuming that pre-coil 316 and post-coil 5 320 are located close to (or at the same distance from) switchable valve device 336, is equal to the travel time of seawater between pre-coil junction 316 and post-coil junction 320, which is mainly determined by delay coil 318.

By adding amounts of the content of bag 310 at registered starting times and switching switchable valve device 336 in predetermined states, controller 37 can measure different travel times of seawater through the entire hydrocarbon measurement module 32 and registering their time of arrival at the underwater mass spectrometer 342.

Sensitivity Calibration

In some embodiments, sensitivity calibration determines the relationship between ion currents inside the underwater mass spectrometer 342 and the concentration of the hydrocarbons in the received and analyzed sample. One possible scheme employed relies on switching switchable valve device 336 between background bag 338 which contains seawater which is, e.g., equilibrated with 100% Nitrogen, and live bag 340 which, for instance, contains a calibrated solution of one or more of Methane, Ethane, Propane and Butane. Controller 37 may be configured to control switchable valve device 336 to add a pulse shaped amount of hydrocarbon content from live bag 340. In this way, device 336 may act as a rinse for the underwater mass spectrometer 342 when it becomes saturated by very high levels of hydrocarbons and is still reading well after the peak has passed.

Figure 4D:
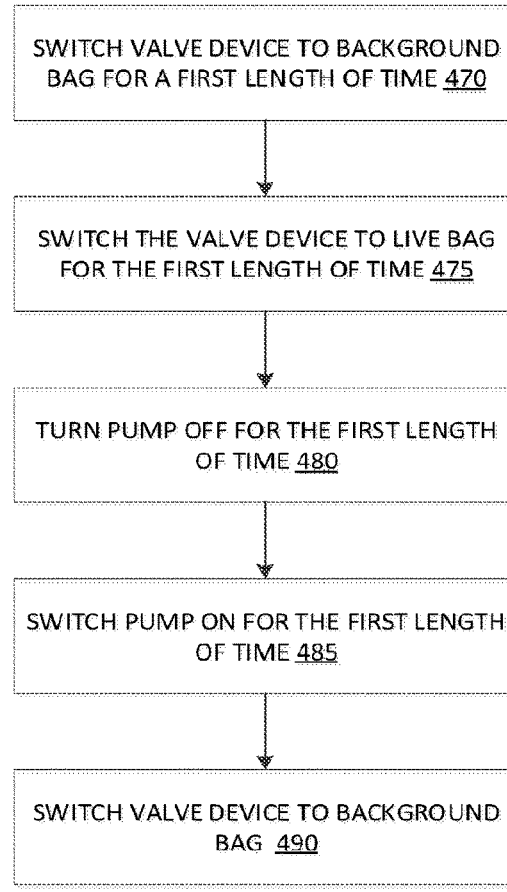

An example method of sensitivity calibration is illustrated below and in FIG. 4D.

At block 470, switchable valve device 336 can switch to background bag 338 for a predetermined amount of time, (e.g., 4 mins);

At block 475, switchable valve device 336 can switch to the live bag 340 for an approximate equivalent amount of time, (e.g., 4 mins);

At block 480, pump 360 can turn off e.g., for an equivalent amount of time. This stops the fluid in front of a membrane present in underwater mass spectrometer 342. The result is that all gases are drained from the contact area within a few seconds to provide an instrument baseline reading;

At block 485, pump 360 can be switched on, e.g., for an approximate equivalent amount of time; and At block 490, switchable valve device 336 can switch to background bag 338.

These predetermined times may be different and also be different for background bag 338 and live bag 340.

The data obtained from the sensitivity calibration may be analyzed by controller 37 on board of remotely operated vehicle 30 and fitted to a functional form to describe the membrane geometry of underwater mass spectrometer 342. This exercise yields the sensitivity for the analytes of interest, in this example: hydrocarbon molecules with 1 to 4 C atoms. Such actions may, alternatively or additionally, also be performed by controller 45 or by any other controller.

Figure 4E:
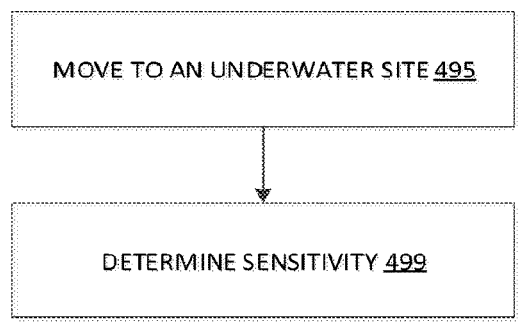

A method of sensitivity calibration of hydrocarbon measurement module 32 is illustrated below and shown in FIG. 4E.

At block 495, the hydrocarbon measurement module can be moved to an underwater site. In some examples, providing at least a portion of the further certified solution of hydrocarbons and at least a portion of the water of the predetermined composition into the sensing loop 304 during the in-situ sensitivity calibration is performed.

At block 499, sensitivity of the mass spectrometer 342 for hydrocarbon components present in the further certified solution of hydrocarbons can be determined.

The third travel time of seawater between pre-coil junction 316 and post-coil 20 junction 320 can be adjusted by changing the length and/or cross section of delay coil 318.

Real-Time Measurements

The system enables real-time in-situ calibrated measurements of dissolved hydrocarbons.

In some examples, controller 37 is configured to receive location data from transponder 39 relative to survey vessel 50. From this location data, controller 37 calculates its 3D position and 3D speed relative to survey vessel 50 in real-time. Relative 3D position and 3D speed data is then sent from controller 37 to controller 45 on board of survey vessel 50. Controller 45 is configured to measure the 3D position and 3D speed of survey vessel 50 based on navigation signals received from one or more satellites 55 using any possible method known in the art. Based on this relative 3D position and 3D speed data of remotely operated vehicle 30 and 3D position and 3D speed of survey vessel 50, controller 45 can then calculate the "absolute" position, and possibly speed, data of remotely operated vehicle 30 as a function of time. Controller 45 can store this historical position data of remotely operated vehicle 30 in any suitable memory as a function of time and display it, for example, monitors, printers, etc.

The remotely operated vehicle 30 moves around at a site, e.g., at a seafloor, an ocean floor or lake floor. Sonar 34 can have a high acoustic sensitivity to bubble clouds originating from the seafloor because it can be located in close proximity to the seafloor. Sonar 34 can detect sound as generated by such bubble clouds and transmits a sonar signal to controller 37 indicative of this bubble sound. Controller 37 is configured to transmitted this sonar signal, or another signal derived from it, to controller 45 on board of survey vessel 50. Controller 45 is configured to show this sonar data to staff, e.g., via a monitor or via a printout. Both controller 37 and 45 may be configured to store the sonar data in suitable memory as a function of time. Staff can decide to operate controller 45 to send a driving signal to controller 37 to control propulsion equipment 31 to steer remotely operated vehicle 30 to the source of the bubble cloud. This may also be done automatically by controller 37 of remotely operated vehicle 30 based on these sonar data. The above explained calibration measurements have provided controller 37 with accurate delay time of seawater entering the system at inlet 306 and arriving at underwater mass spectrometer 342 via junction 316. When underwater mass spectrometer 342 detects and measures a certain amount of hydrocarbons in the received sample it sends hydrocarbon content data to controller 37. Controller 37 receives the hydrocarbon content data as a function of time. Depending on the underwater mass spectrometer 342 used, this data will indicate presence of at least one of methane, ethane, propane, and butane. Underwater mass spectrometer 342 may be configured to only send such hydrocarbon content data if the concentration of one of these mentioned hydrocarbons exceeds a predetermined threshold.

Controller 37 is, in some embodiments, configured to share such hydrocarbon content data with controller 45 such that it can be displayed, for example, via a suitable display or print on paper. Both controller 37 and 45 may be configured to store the hydrocarbon content data in suitable memory as a function of time.

By taking the above explained first travel time between inlet 306 and underwater mass spectrometer 342 into account, controller 37 and/or controller 45 can calculate the location at which location remotely operated vehicle 30 received the detected and measured hydrocarbons in seawater. Controller 37 and/or controller 45 can also determine the time when this happened. From these data, controller 37 and/or controller 45 can map a dissolved hydrocarbon plume in real time allowing staff to redirect remotely operated vehicle 30 back into a most prospective areas for further, detailed measurements. As an alternative, controller 37 and/or 45 may be configured to automatically redirect remotely operated vehicle 30 back into a most prospective area for further, detailed measurements based on the calculated location (and possibly time) where remotely operated vehicle 30 received the detected and measured hydrocarbons in seawater.

Today, commercially available underwater mass spectrometers do not provide instantaneous or near-instantaneous measurement results. They need a certain measurement time to be able to provide a measurement signal to controller 37. For instance, the time necessary for the sample to flow from pre-coil junction 316 to underwater mass spectrometer 342 and the measurement time to detect methane may be, for instance, 8 sec in total. In some embodiments, pump 324 and the delay coil 318 are configured to provide an equal delay time of, for example, 8 seconds to the flow of seawater between pre-coil junction 316 and postcoil junction 320. Once underwater mass spectrometer 342 has detected methane, or any other predetermined hydrocarbon, in the received sample and has sent measurement data to that effect to controller 37, controller 37 may be configured to switch switchable valve device 336 to connect conduit 354 to conduit 352 and no longer to conduit 350 so further samples of seawater are taken at the location of post-coil junction 320. In some examples, the further samples can be larger than the sample taken from main loop 302 at the location of pre-coil junction 316. The larger further sample flows to underwater mass spectrometer 342 which then can perform a more thorough measurement to generate a more detailed analysis of the hydrocarbon content of the seawater. This, then, provides the underwater mass spectrometer 342 with more time to detect heavier hydrocarbon molecules in the sample, like ethane, propane, and butane, and possibly others.

In these embodiments, the delay time of seawater flowing from pre-coil junction 316 to post-coil junction 320 is configured to be substantially equal to the total time that a sample flows from pre-coil junction 316 to underwater mass spectrometer 342 and the measurement time of underwater mass spectrometer 342. Therefore, in this embodiment, controller 37 is configured to control switchable valve device 336 such that the further larger sample is taken from seawater flowing in main loop 302 which originates from the same location in the surrounding seawater as from which the earlier smaller sample was taken via pre-coil junction 316.

Note also that the delay time of the delay coil 318, as well as several travel times of seawater flowing in the system have been measured in real-time during the calibration process as indicated above, such that actual, real-time values are known to controller 37 and/or controller 45. Taking these delay times and travel times into account, controller 37 can switch switchable valve device 336 such that the earlier smaller sample originates from, substantially, the same location in the surrounding seawater as the later larger sample.

So, when the remotely operated vehicle 30 is controlled by controllers 37 and/or 45 to be redirected into a prospective area of a hydrocarbon plume in the surrounding seawater, there is a high likelihood that hydrocarbon measurement module 32 successfully traps segments of fluid measured to have the highest hydrocarbon concentrations along its path and to provide the on-board underwater mass spectrometer 342 sufficient time to quantify the hydrocarbons present.

In some embodiments, controller 37 is configured to control switchable valve device 344 to connect conduit 362, in which the sample flows as analysed by underwater mass spectrometer 342, to at least one of its output conduits 364, 366, 368 and 370.

When conduit 362 is connected to output conduit 364, the sample will be exhausted in main loop 314, e.g. downstream from pump 324 and upstream from flow measurement device 328.

When conduit 362 is connected to output conduit 366, the sample will be exhausted as waste inside the body of remotely operated vehicle 30.

When conduit 362 is connected to output conduit 368 or 370, respectively, the sample 25 will be exhausted in sample bag 348 or sample bag 346, respectively.

Controller 37 may be programmed to automatically switch switchable valve device 344 such that conduit 362 is connected to either one of conduits 368 or 370 when underwater mass spectrometer 342 has measured a certain hydrocarbon content above a predetermined threshold. The sample collected in the sample bags 346, 348 can then be transported to the survey vessel 50 for further analysis in a laboratory.

Methane sensor 322, if present, can be used for redundant measurement. For example, methane sensor 322 is configured to transmit methane measurement data to controller 37 which then may store such data as a function of time and forward them to controller 45, for example, to be displayed. Such methane measurement data from methane sensor 322 may be used to validate and/or support measurements made by underwater mass spectrometer.

Oxygen measurement device 330 is configured to measure dissolved oxygen. As explained above, the underwater mass spectrometer 342 also measures 5 dissolved oxygen, so this redundant measurement may be used to ensure that the underwater mass spectrometer 342 is working properly.

Figure 5:
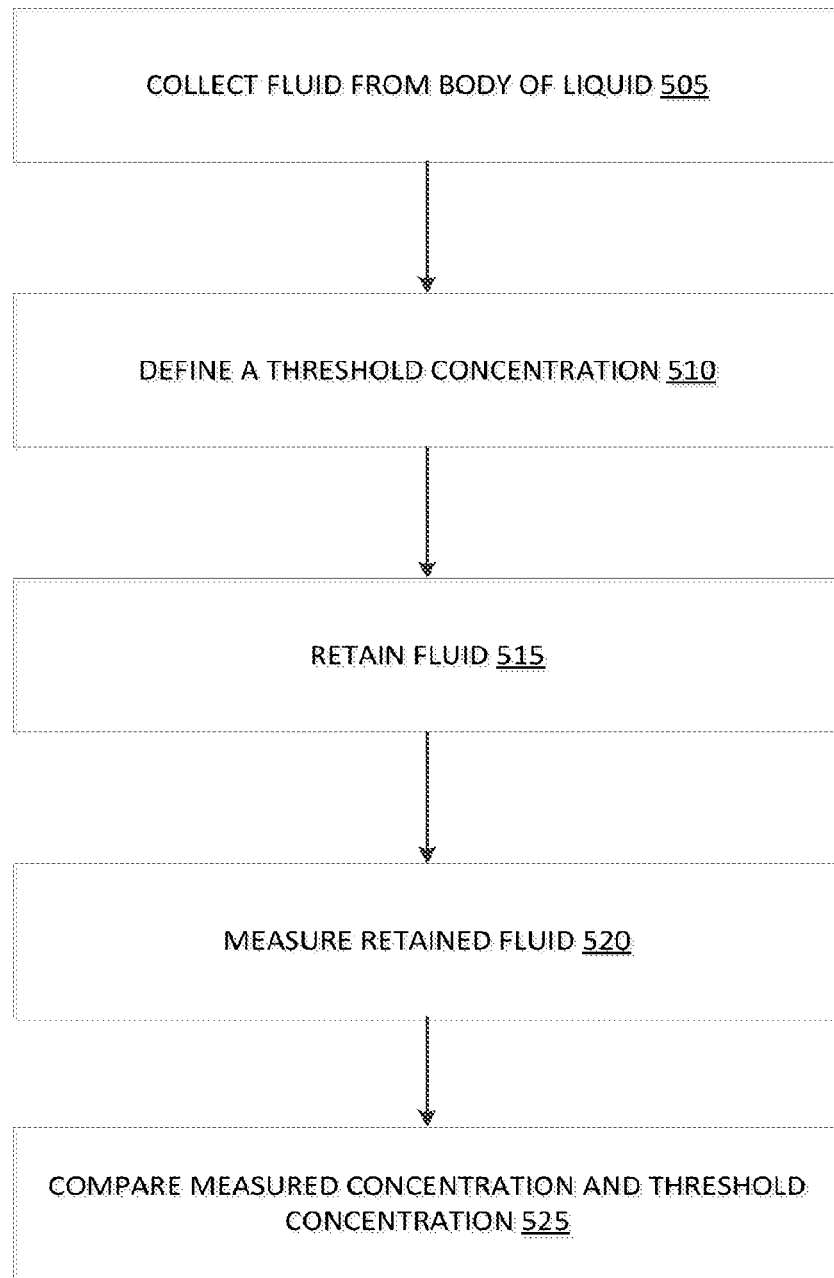
FIG. 5 shows a flow diagram of analyzing fluid samples, in accordance with an example embodiment.

Further disclosed is an example method to provide in situ analysing fluid samples in a body of water, for example, from a river, lake or ocean. The method is illustrated in FIG. 5 and below.

At block 505, fluid is collected continuously from the body of water into a fluid circuit. It will be understood that a fluid sample collected from the floor of the body of water will fall within the meaning of collecting from the body of water.

At block 510, a threshold concentration for a target analyte is defined. The target analyte may be, for example, without limitation, hydrocarbons, preferably C1-C5 hydrocarbons, atmospheric gases, preferably helium, argon, carbon dioxide, and/or bio-markers. Preferably, the target analyte is indicative of a hydrocarbon content of a bulk portion of the body of water. In a preferred embodiment, the target analyte is methane. In another embodiment of the present invention, the method is used to infer the presence of an active hydrocarbon seep. In this case, the active hydrocarbon seep is inferred by a measured analyte concentration exceeding the threshold concentration.

At block 515, fluid is retained in the fluid circuit in a time-ordered fashion. In some examples, the fluid is collected and retained in laminar flow. At block 520, the concentration of the target analyte is measured within the fluid circuit. The fluid sample may be analysed, for example, using a mass spectrometer, Raman spectroscopy, isotope probes, a fluorometer, and combinations thereof.

At block 525, the measured concentrations are compared to the threshold concentration. When one or more of the measured concentrations is greater than the threshold concentration, further analysis is conducted on the retained fluid. Specifically, when a sample from time or location, $t_n$ or $d_n$, has a measured concentration that exceeds the threshold concentration, further analysis is conducted on the corresponding retained fluid that was collected at $t_n$ or $d_n$. This can be accomplished, for example, when the fluid circuit has a length of tubing that allows for analysing a target analyte at an end closer to the front end of the fluid circuit and then capturing or analysing the time-ordered retained fluid at an end closer to the rear end of the fluid circuit.

In one embodiment, the tubing may be coiled. In another embodiment, the collected fluid may be separated into a sensing portion and a retained portion. Preferably, both the sensing portion and the retained portion are maintained under laminar flow conditions.

As an example, the target analyte may be methane and the further analysis may be isotope analysis, concentration of ethane or higher hydrocarbons, and the like. The presence of methane and ethane, for example, may be used to infer the presence of an active hydrocarbon seep.

An alternative or complementary example method the above, is described below.

A method for in situ analyzing fluid samples in a body of water, the method comprising: defining a target analyte and a threshold concentration for the target analyte; continuously collecting fluid from the body of water into a fluid circuit; retaining the fluid in the fluid circuit in a time-ordered fashion; measuring the concentrations of the target analyte within the fluid circuit; comparing each of the measured concentrations to the threshold concentration; and when one or more of the measured concentrations is greater than the threshold concentration, conducting further analysis on the time-ordered retained fluid.

In some examples, the fluid is collected in laminar flow. In some examples, the fluid can be separated into a sensing portion and a retained portion. The sensing portion and the retained portion can be maintained under laminar flow conditions.

In some examples, fluid sample is analyzed using a mass spectrometer, Raman spectroscopy, isotopes probes, a fluorometer, and combinations thereof.

In some examples, the further analysis can include an analysis of fluid components other than the target analyte.

In some examples, the fluid circuit can be a length of tubing. In some examples, the target analyte can be indicative of the hydrocarbon content of a bulk portion of the body of water. In some examples, the target analyte is methane. In some examples, the presence of an active hydrocarbon seep is determined when the measured analyte concentration exceeds the threshold concentration.

In some examples, the analysis is conducted in a subsurface vehicle. In other examples, the analysis is conducted on a surface vessel.

In some examples, the target analyte is selected from hydrocarbons, preferably C1-C5 hydrocarbons, atmospheric gases, preferably helium, argon, carbon dioxide, bio-markers and combinations thereof. In some examples, the hydrocarbons are selected from the group consisting of C1, C2, C3, C4, and C5 hydrocarbons and combinations thereof. 15. The method of clause 1, wherein the body of water is selected from rivers, lakes, and oceans. In some examples, the fluid sample is a sample of pore water collected from a floor of the body of water.

Figure 6:
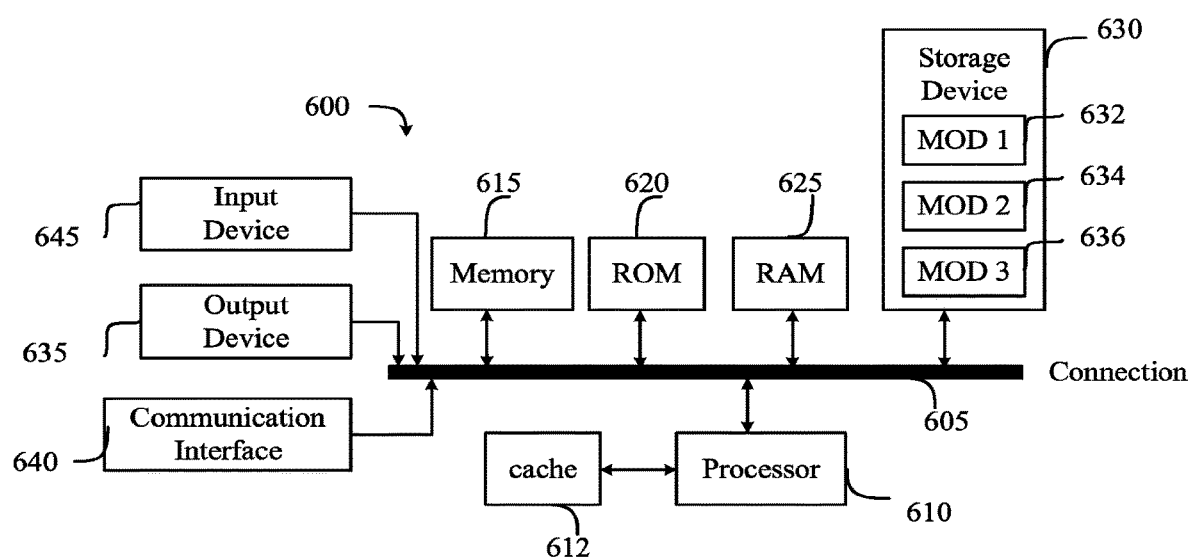
FIG. 6 show a block diagram of an example system, in accordance with an example embodiment.

FIG. 6 illustrates a computing system architecture 600 including various components in electrical communication with each other using a connection 606, such as a bus. Example system architecture 600 includes a processing unit (CPU or processor) 604 and a system connection 606 that couples various system components including the system memory 620, such as read only memory (ROM) 618 and random access memory (RAM) 616, to the processor 604. The system architecture 600 can include a cache 602 of high-speed memory connected directly with, in close proximity to, or integrated as part of the processor 604. The system architecture 600 can copy data from the memory 620 and/or the storage device 608 to the cache 602 for quick access by the processor 604. In this way, the cache can provide a performance boost that avoids processor 604 delays while waiting for data. These and other modules can control or be configured to control the processor 604 to perform various actions.

Other system memory 620 may be available for use as well. The memory 620 can include multiple different types of memory with different performance characteristics. The processor 604 can include any general purpose processor and a hardware or software service, such as service 1 610, service 2 612, and service 3 614 stored in storage device 608, configured to control the processor 604 as well as a special-purpose processor where software instructions are incorporated into the actual processor design. The processor 604 may be a completely self-contained computing system, containing multiple cores or processors, a bus, memory controller, cache, etc. A multi-core processor may be symmetric or asymmetric.

To enable user interaction with the computing system architecture 600, an input device 622 can represent any number of input mechanisms, such as a microphone for speech, a touch-sensitive screen for gesture or graphical input, keyboard, mouse, motion input, speech and so forth. An output device 624 can also be one or more of a number of output mechanisms known to those of skill in the art. In some instances, multimodal systems can enable a user to provide multiple types of input to communicate with the computing system architecture 600. The communications interface 626 can generally govern and manage the user input and system output. There is no restriction on operating on any particular hardware arrangement and therefore the basic features here may easily be substituted for improved hardware or firmware arrangements as they are developed.

Storage device 608 is a non-volatile memory and can be a hard disk or other types of computer readable media which can store data that are accessible by a computer, such as magnetic cassettes, flash memory cards, solid state memory devices, digital versatile disks, cartridges, random access memories (RAMs) 616, read only memory (ROM) 618, and hybrids thereof.

The storage device 608 can include services 610, 612, 614 for controlling the processor 604. Other hardware or software modules are contemplated. The storage device 608 can be connected to the system connection 606. In one aspect, a hardware module that performs a particular function can include the software component stored in a computer-readable medium in connection with the necessary hardware components, such as the processor 604, connection 606, output device 624, and so forth, to carry out the function.

CLAUSES

1. An hydrocarbon measurement module comprising:
   a main loop having a water inlet (306) for receiving water, a first pump (324) for pumping said received water through said main loop;
   a sensing loop (304) having a first conduit (350) connected to said main loop at a first junction (316) and configured to receive a sample of said water flowing in said main loop, a second pump (360) for pumping said sample through said sensing loop (304), and a mass spectrometer (342) configured to analyse said sample and detect if said sample contains one or more predetermined hydrocarbons.
2. The hydrocarbon measurement module according to claim 1, wherein said first pump (324) is configured to pump said water as a continuous laminar flow through said main loop.
3. The hydrocarbon measurement module according to claim 1 or 2, comprising a timing calibration bag (310) which is connected to the inlet (306) of the main loop and comprises a certified solution of hydrocarbons, and is configured to provide at least a portion of said certified solution of hydrocarbon to said inlet (306) during an in-situ timing calibration in which at least a first travel time is determined of said certified solution of hydrocarbon flowing from said inlet (306) to said mass spectrometer (342).
4. The hydrocarbon measurement module according to claim 1, 2 or 3, comprising a first sensitivity calibration bag (340) and a second sensitivity calibration bag (358) which are both arranged in the sensing loop (304), the first sensitivity calibration bag (340) comprising a further certified solution of hydrocarbons and the second sensitivity calibration bag (338) comprising water of a predetermined composition, the hydrocarbon measurement module being configured to alternately provide at least a portion of said further certified solution of hydrocarbon and at least a portion of said water of said predetermined composition into said sensing loop (304) during an in-situ sensitivity calibration in which sensitivity of said mass spectrometer (342) for hydrocarbon components present in said further certified solution of hydrocarbon is determined.
5. The hydrocarbon measurement module according to any of the preceding claims, comprising a delay coil (318) arranged in said main loop (314), said first junction (316) being arranged upstream from said delay coil (318), the sensing loop (304) comprising a second conduit (352) connected to said main loop at a second junction (320) located downstream from said delay coil (318) and configured to receive a further sample from said water flowing in said main loop via said second junction (320), the mass spectrometer (342) being configured to analyse said further sample and detect if said further sample contains one or more predetermined hydrocarbons.
6. The hydrocarbon measurement module according to claim 5, comprising a controller (37) and a switching unit (336), said controller (37) being at least connected to said switching unit (336) and to said mass spectrometer (342), said first conduit (350) and second conduit (352) being both connected to said switching unit (336) and said switching unit (336) being connected to said mass spectrometer (342), wherein said controller is configured to control said switching unit (336) to send said sample as received from said first conduit (350) to said mass spectrometer (342), which mass spectrometer (342) is configured to provide a trigger signal to said controller (37) once it detects a predetermined amount of hydrocarbon in said sample and said controller is configured to control said switching unit (336) to send said further sample as received from said second conduit (352) to said mass spectrometer (342) at a predetermined time after receiving said trigger signal taking into account delay time caused by said delay coil (318).
7. The hydrocarbon measurement module according to any of the preceding claims, wherein the sensing loop (304) comprises a further switching unit (344) arranged downstream from said mass spectrometer (342) and configured to receive exhaust water from an outlet of said mass spectrometer (342) and forward said exhaust water to at least one of a sample bag (346; 348), a waste outlet, and a junction (326) in said main loop.
8. The hydrocarbon measurement module according to any of the preceding claims, comprising at least one of a methane measurement device (322), a flow measurement device (328, and an oxygen concentration measurement device (330).
9. An underwater vehicle comprising a hydrocarbon measurement module according to any of the preceding claims.
10. The underwater vehicle according to claim 9, comprising a sonar (34), the underwater vehicle being configured to detect hydrocarbon seeps close to at least one of a bottom of a sea, ocean and lake.
11. A method of in-situ timing calibration of a hydrocarbon measurement module, which hydrocarbon measurement module comprises:
   a main loop having a water inlet (306) for receiving water, a first pump (324) for pumping said received water through said main loop;
   a sensing loop (304) having a conduit (350) connected to said main loop at a junction (316) and configured to receive a sample of said water flowing in said main loop, a second pump (360) for pumping said sample through said sensing loop (304), and a mass spectrometer (342) configured to analyse said sample and detect if said sample contains one or more predetermined hydrocarbons;
   a timing calibration bag (310) which is connected to the inlet (306) of the main loop and comprises a certified solution of hydrocarbons;

the method including the following actions:
  moving said hydrocarbon measurement module to an underwater site;
  controlling said timing calibration bag (310) to provide at least a portion of said certified solution of hydrocarbons to said inlet (306) during said in-situ timing calibration; and
  determining at least a travel time from said certified solution of hydrocarbon flowing from said inlet (306) to said mass spectrometer (342) via said junction (316) based on hydrocarbon analysis by said mass spectrometer (342).

12. A method of in-situ timing calibration of a hydrocarbon measurement module, which hydrocarbon measurement module comprises:
  a main loop having a water inlet (306) for receiving water, a first pump (324) for pumping said received water through said main loop;
  a sensing loop (304) having a first conduit (350) connected to said main loop at a first junction (316) and configured to receive a sample of said water flowing in said main loop, a second pump (360) for pumping said sample through said sensing loop (304);
  a timing calibration bag (310) which is connected to the inlet (306) of the main loop and comprises a certified solution of hydrocarbons
  a delay coil (318) arranged in said main loop (314), said first junction (316) being arranged upstream from said delay coil (318), the hydrocarbon measurement module (30) comprising a second conduit (352) connected to said main loop at a second junction (320) located downstream from said delay coil (318) and configured to receive a further sample from said water flowing in said main loop;
  a mass spectrometer (342) configured to analyse said sample and further sample and detect if said sample and further sample contain one or more predetermined hydrocarbons;
  the method including the following actions:
moving said hydrocarbon measurement module to an underwater site;
  controlling said timing calibration bag (310) to provide at least a portion of said certified solution of hydrocarbon to said inlet (306) during said in-situ timing calibration; and
  determining at least a delay time caused by said delay coil (318) from said certified solution of hydrocarbon flowing from said inlet (306) to said mass spectrometer (342) either via said first conduit (350) or said second conduit (352) based on hydrocarbon analysis by said mass spectrometer (342).

13. A method of sensitivity calibration of a hydrocarbon measurement module comprising, which hydrocarbon measurement module comprises:
  a main loop having a water inlet (306) for receiving water, a first pump (324) for pumping said received water through said main loop;
  a sensing loop (304) having a first conduit (350) connected to said main loop at a first junction (316) and configured to receive a sample of said water flowing in said main loop, a second pump (360) for pumping said sample through said sensing loop (304), and a mass spectrometer (342) configured to analyse said sample and detect if said sample contains one or more predetermined hydrocarbons;
  a first sensitivity calibration bag (340) and a second sensitivity calibration bag (358) which are both arranged in the sensing loop (304), the first sensitivity calibration bag (340) comprising a further certified solution of hydrocarbons and the second sensitivity calibration bag (338) comprising water of a predetermined composition;
  the method including the actions of:
    moving said hydrocarbon measurement module to an underwater site;
    alternately providing at least a portion of said further certified solution of hydrocarbons and at least a portion of said water of said predetermined composition into said sensing loop (304) during said in-situ sensitivity calibration;
    determining sensitivity of said mass spectrometer (342) for hydrocarbon components present in said further certified solution of hydrocarbons based on hydrocarbon analysis by said mass spectrometer (342).

14. A method of using the hydrocarbon measurement module as defined in any of the claims 1-8 or the underwater vehicle as defined in any of the claims 9-10, after having performed the method of any of the claims 11-13.

15. A method of operating a hydrocarbon measurement module, the hydrocarbon measurement module comprising:
  a main loop having a water inlet (306) for receiving water, a first pump (324) for pumping said received water through said main loop;
  a sensing loop (304) having a first conduit (350) connected to said main loop at a first junction (316) and configured to receive a sample of said water flowing in said main loop, a second pump (360) for pumping said sample through said sensing loop (304), and a mass spectrometer (342) configured to analyse said sample and detect if said sample contains one or more predetermined hydrocarbons;
  a delay coil (318) arranged in said main loop (314), said first junction (316) being arranged upstream from said delay coil (318), the sensing loop (304) comprising a second conduit (352) connected to said main loop at a second junction (320) located downstream from said delay coil (318) and configured to receive a further sample from said water flowing in said main loop via said second junction (320), the mass spectrometer (342) being configured to analyse said further sample and detect if said further sample contains one or more predetermined hydrocarbons;
  a controller (37) and a switching unit (336), said controller being at least connected to said switching unit (336) and to said mass spectrometer (342), said first conduit (350) and second conduit (352) being both connected to said switching unit (336), and said switching unit (336) being connected to said mass spectrometer (342);
  the method including the actions of:
    moving said hydrocarbon measurement module to an underwater site;
    controlling said switching unit (336) to send said sample as received from said first conduit (350) to said mass spectrometer (342),
    receiving from said mass spectrometer (342) a trigger signal once it detects a predetermined amount of methane in said sample; and
    controlling said switching unit (336) to forward said further sample as received from said second conduit (352) to said mass spectrometer (342) at a predetermined time after receiving said trigger signal taking into account delay time caused by said delay coil (318).

For clarity of explanation, in some instances the present technology may be presented as including individual functional blocks including functional blocks comprising devices, device components, steps or routines in a method embodied in software, or combinations of hardware and software.

In some embodiments the computer-readable storage devices, mediums, and memories can include a cable or wireless signal containing a bit stream and the like. However, when mentioned, non-transitory computer-readable storage media expressly exclude media such as energy, carrier signals, electromagnetic waves, and signals per se.

Methods according to the above-described examples can be implemented using computer-executable instructions that are stored or otherwise available from computer readable media. Such instructions can comprise, for example, instructions and data which cause or otherwise configure a general purpose computer, special purpose computer, or special purpose processing device to perform a certain function or group of functions. Portions of computer resources used can be accessible over a network. The computer executable instructions may be, for example, binaries, intermediate format instructions such as assembly language, firmware, or source code. Examples of computer-readable media that may be used to store instructions, information used, and/or information created during methods according to described examples include magnetic or optical disks, flash memory, USB devices provided with non-volatile memory, networked storage devices, and so on.

Devices implementing methods according to these disclosures can comprise hardware, firmware and/or software, and can take any of a variety of form factors. Typical examples of such form factors include laptops, smart phones, small form factor personal computers, personal digital assistants, rackmount devices, standalone devices, and so on. Functionality described herein also can be embodied in peripherals or add-in cards. Such functionality can also be implemented on a circuit board among different chips or different processes executing in a single device, by way of further example.

The instructions, media for conveying such instructions, computing resources for executing them, and other structures for supporting such computing resources are means for providing the functions described in these disclosures.

The example methods provided herein are by way of example, as there are a variety of ways to carry out the method. Additionally, while the example methods are illustrated with a particular order of steps, those of ordinary skill in the art will appreciate that methods and the steps illustrated therein can be executed in any order that accomplishes the technical advantages of the present disclosure and can include fewer or more steps than illustrated.

Variations to the disclosed embodiments can be understood and effected by a person skilled in the art in practicing the claimed invention, from a study of the figures, the description and the attached claims. In the description and claims, the word "comprising" does not exclude other elements, and the indefinite article "a" or "an" does not exclude a plurality. In fact it is to be construed as meaning "at least one". The mere fact that certain features are recited in mutually different dependent claims does not indicate that a combination of these features cannot be used to advantage. Any reference signs in the claims should not be construed as limiting the scope of the invention. Features of the above described embodiments and aspects can be combined unless their combining results in evident technical conflicts.

We claim:

1. A hydrocarbon measurement module comprising:
   a main loop having a water inlet for receiving water, a first pump for pumping the received water through the main loop;
   a sensing loop having a first conduit connected to the main loop at a first junction and configured to receive a sample of the water flowing in the main loop, a second pump for pumping the sample through the sensing loop;
   a mass spectrometer configured to analyze the sample and detect if the sample contains one or more predetermined hydrocarbons; and
   a timing calibration bag connected to the water inlet of the main loop, the timing calibration bag including a certified solution of hydrocarbons and configured to provide at least a portion of the certified solution of hydrocarbons to the water inlet during an in-situ timing calibration in which at least a first travel time is determined of the certified solution of hydrocarbon flowing from the water inlet to the mass spectrometer.

2. The hydrocarbon measurement module according to claim 1, wherein the first pump is configured to pump the water as a continuous laminar flow through the main loop.

3. The hydrocarbon measurement module according to claim 1, further comprising a first sensitivity calibration bag and a second sensitivity calibration bag which are both arranged in the sensing loop, the first sensitivity calibration bag comprising a further certified solution of hydrocarbons and the second sensitivity calibration bag comprising water of a predetermined composition, the hydrocarbon measurement module being configured to alternately provide at least a portion of the further certified solution of hydrocarbon and at least a portion of the water of the predetermined composition into the sensing loop during an in-situ sensitivity calibration in which sensitivity of the mass spectrometer for hydrocarbon components present in the further certified solution of hydrocarbon is determined.

4. The hydrocarbon measurement module according to claim 1, further comprising a delay coil arranged in the main loop, the first junction being arranged upstream from the delay coil, the sensing loop comprising a second conduit connected to the main loop at a second junction located downstream from the delay coil and configured to receive a further sample from the water flowing in the main loop via the second junction, the mass spectrometer being configured to analyse the further sample and detect if the further sample contains one or more predetermined hydrocarbons.

5. The hydrocarbon measurement module according to claim 4, further comprising a controller and a switching unit, the controller being at least connected to the switching unit and to the mass spectrometer, the first conduit and second conduit being both connected to the switching unit and the switching unit being connected to the mass spectrometer, wherein the controller is configured to control the switching unit to send the sample as received from the first conduit to the mass spectrometer, which mass spectrometer is configured to provide a trigger signal to the controller once it detects a predetermined amount of hydrocarbon in the sample and the controller is configured to control the switching unit to send the further sample as received from the second conduit to the mass spectrometer at a predetermined time after receiving the trigger signal taking into account delay time caused by the delay coil.

6. The hydrocarbon measurement module according to claim 1, wherein the sensing loop comprises a further switching unit arranged downstream from the mass spectrometer and configured to receive exhaust water from an outlet of the mass spectrometer and forward the exhaust water to at least one of a sample bag, a waste outlet, and a junction in the main loop.

7. The hydrocarbon measurement module according to claim 1, further comprising at least one of a methane measurement device, a flow measurement device, and an oxygen concentration measurement device.

8. The hydrocarbon measurement module according to claim 1, wherein the module is included in an underwater vehicle.

9. An underwater vehicle comprising:
a hydrocarbon measurement module comprising:
   a main loop having a water inlet for receiving water, a first pump for pumping the received water through the main loop;
   a sensing loop having a first conduit connected to the main loop at a first junction and configured to receive a sample of the water flowing in the main loop, a second pump for pumping the sample through the sensing loop;
   a mass spectrometer configured to analyze the sample and detect if the sample contains one or more predetermined hydrocarbons; and
   a timing calibration bag connected to the water inlet of the main loop, the timing calibration bag including a certified solution of hydrocarbons and configured to provide at least a portion of the certified solution of hydrocarbons to the water inlet during an in-situ timing calibration in which at least a first travel time is determined of the certified solution of hydrocarbon flowing from the water inlet to the mass spectrometer.

10. The underwater vehicle according to claim 9, wherein the sensing loop comprises a further switching unit arranged downstream from the mass spectrometer and configured to receive exhaust water from an outlet of the mass spectrometer and forward the exhaust water to at least one of a sample bag, a waste outlet, and a junction in the main loop.

11. The underwater vehicle according to claim 9, comprising a sonar, the underwater vehicle being configured to detect hydrocarbon seeps close to at least one of a bottom of a sea, ocean and lake.

12. The underwater vehicle according to claim 9, wherein the first pump is configured to pump the water as a continuous laminar flow through the main loop.

13. The underwater vehicle according to claim 9, further comprising a first sensitivity calibration bag and a second sensitivity calibration bag which are both arranged in the sensing loop, the first sensitivity calibration bag comprising a further certified solution of hydrocarbons and the second sensitivity calibration bag comprising water of a predetermined composition, the hydrocarbon measurement module being configured to alternately provide at least a portion of the further certified solution of hydrocarbon and at least a portion of the water of the predetermined composition into the sensing loop during an in-situ sensitivity calibration in which sensitivity of the mass spectrometer for hydrocarbon components present in the further certified solution of hydrocarbon is determined.

14. The underwater vehicle according to claim 9, further comprising a delay coil arranged in the main loop, the first junction being arranged upstream from the delay coil, the sensing loop comprising a second conduit connected to the main loop at a second junction located downstream from the delay coil and configured to receive a further sample from the water flowing in the main loop via the second junction, the mass spectrometer being configured to analyse the further sample and detect if the further sample contains one or more predetermined hydrocarbons.

15. The underwater vehicle according to claim 14, further comprising a controller and a switching unit, the controller being at least connected to the switching unit and to the mass spectrometer, the first conduit and second conduit being both connected to the switching unit and the switching unit being connected to the mass spectrometer, wherein the controller is configured to control the switching unit to send the sample as received from the first conduit to the mass spectrometer, which mass spectrometer is configured to provide a trigger signal to the controller once it detects a predetermined amount of hydrocarbon in the sample and the controller is configured to control the switching unit to send the further sample as received from the second conduit to the mass spectrometer at a predetermined time after receiving the trigger signal taking into account delay time caused by the delay coil.

16. The underwater vehicle according to claim 9, comprising at least one of a methane measurement device, a flow measurement device, and an oxygen concentration measurement device.

17. A method comprising:
pumping, by a first pump through a main loop, water received for a water inlet of the main loop;
receiving a sample of the water flowing in the main loop at a sensing loop, the sensing loop having a first conduit connected to the main loop at a first junction and a second pump for pumping the sample through the sensing loop;
analyzing the sample at a mass spectrometer to detect if the sample contains one or more predetermined hydrocarbons; and
providing at least a portion of certified solution of hydrocarbons to the water inlet during an in-situ timing calibration in which at least a first travel time is determined of the certified solution of hydrocarbons flowing from the water inlet to the mass spectrometer, wherein the certified solution of hydrocarbons are stored in a timing calibration bag connected to the water inlet of the main loop.

18. The method according to claim 17, wherein the first pump is configured to pump the water as a continuous laminar flow through the main loop.

19. The method according to claim 17, wherein the main loop, the sensing loop and the mass spectrometer are part of a hydrocarbon measurement module included in an underwater vehicle.

20. The method according to claim 19, wherein the underwater vehicle includes a sonar configured to detect hydrocarbon seeps close to at least one of a bottom of a sea, ocean and lake.

* * * * *